(12) United States Patent
West et al.

(10) Patent No.: US 9,435,720 B2
(45) Date of Patent: Sep. 6, 2016

(54) MULTIPLE SLIDE PROCESSING APPARATUS

(71) Applicant: Hardy Diagnostics, Santa Maria, CA (US)

(72) Inventors: Jerry West, Ovilla, TX (US); Randy Thomas, Jay, OK (US); Jeff Gibbs, Wichita Falls, TX (US); Lee Carter, McKinney, TX (US)

(73) Assignee: Hardy Diagnostics, Santa Maria, CA (US)

(*) Notice: Subject to any disclaimer, the term of this patent is extended or adjusted under 35 U.S.C. 154(b) by 0 days.

(21) Appl. No.: 14/807,990

(22) Filed: Jul. 24, 2015

(65) Prior Publication Data
US 2016/0209301 A1  Jul. 21, 2016

Related U.S. Application Data

(63) Continuation of application No. 13/857,965, filed on Apr. 5, 2013, now Pat. No. 9,091,621.

(51) Int. Cl.
*A61B 10/00* (2006.01)
*G01N 1/30* (2006.01)

(52) U.S. Cl.
CPC ........... *G01N 1/30* (2013.01); *G01N 2001/302* (2013.01)

(58) Field of Classification Search
CPC ................................. A61B 10/00; G01N 1/30
See application file for complete search history.

(56) References Cited

U.S. PATENT DOCUMENTS

| | | | |
|---|---|---|---|
| 3,431,886 A | 3/1969 | Mccormick et al. | |
| 3,837,795 A | 9/1974 | Becker et al. | |
| 4,029,470 A | 6/1977 | Wilkins et al. | |
| 4,088,797 A | 5/1978 | Johnson | |
| 4,120,662 A | 10/1978 | Fosslien | |
| 4,151,809 A | 5/1979 | Johnson | |
| 4,639,421 A | 1/1987 | Sage | |
| 4,665,024 A | 5/1987 | Mansour | |
| 4,950,120 A | 8/1990 | Barnes | |
| 5,009,185 A | 4/1991 | Stokes et al. | |
| 5,081,017 A | 1/1992 | Longoria | |

(Continued)

FOREIGN PATENT DOCUMENTS

| | | |
|---|---|---|
| WO | 9739348 A1 | 10/1997 |
| WO | 0142796 A1 | 6/2001 |
| WO | 2010078177 A | 7/2010 |

OTHER PUBLICATIONS

European Search Report, Application EP 14162285.2, Sep. 11, 2014.

(Continued)

*Primary Examiner* — Jyoti Nagpaul
(74) *Attorney, Agent, or Firm* — SoCal IP Law Group LLP; Guy L. Cumberbatch

(57) ABSTRACT

A slide processing apparatus comprises a slide or processing station which may include a plurality of cuvettes, each cuvette configured to receive a slide. A reagent fluid supply is coupled to each cuvette to deliver and apply reagent for treatment of the slide. A slide gripper is disposed above the slide processing station and is configured to move the slide in and out of the cuvettes. A screw assembly is disposed adjacent the slide processing station, the screw assembly configured to receive a plurality of slides, wherein rotation of the screw assembly advances the plurality of slides for engagement by the slide gripper.

8 Claims, 7 Drawing Sheets

(56) References Cited

U.S. PATENT DOCUMENTS

| | | |
|---|---|---|
| 5,137,810 A | 8/1992 | Sizemore et al. |
| 5,310,043 A | 5/1994 | Alcorn |
| 5,340,719 A | 8/1994 | Hajek et al. |
| 5,424,826 A | 6/1995 | Kinney |
| 5,449,622 A | 9/1995 | Yabe et al. |
| 5,545,535 A | 8/1996 | Roth et al. |
| 5,554,505 A | 9/1996 | Hajek et al. |
| 5,593,886 A | 1/1997 | Gaddy |
| 5,610,198 A | 3/1997 | Barry et al. |
| 5,633,722 A | 5/1997 | Wasinger et al. |
| 5,700,346 A | 12/1997 | Edwards |
| 5,804,141 A | 9/1998 | Chianese |
| 5,827,680 A | 10/1998 | Meszaros et al. |
| 6,056,790 A | 5/2000 | Clark et al. |
| 6,096,271 A | 8/2000 | Bogen et al. |
| 6,149,871 A | 11/2000 | Guirguis et al. |
| 6,495,106 B1 | 12/2002 | Kalra et al. |
| 6,585,936 B1 | 7/2003 | Shah |
| 6,594,537 B1 | 7/2003 | Bernstein et al. |
| 7,226,788 B2 | 6/2007 | De La |
| 7,303,725 B2 | 12/2007 | Reinhardt et al. |
| 7,452,506 B2 | 11/2008 | Gibbs et al. |
| 7,572,638 B2 | 8/2009 | Pressman et al. |
| 7,718,435 B1 | 5/2010 | Bogen et al. |
| 2008/0102006 A1 | 5/2008 | Kram et al. |
| 2011/0091962 A1 | 4/2011 | Carsillo et al. |

OTHER PUBLICATIONS

Extended European Search Report, Application EP 14162285.2, Jan. 14, 2015.
Joklik et al., Zinsser Microbiology, 18th edition (1984), pp. 19-20. Prentice-Hall, Inc., USA.

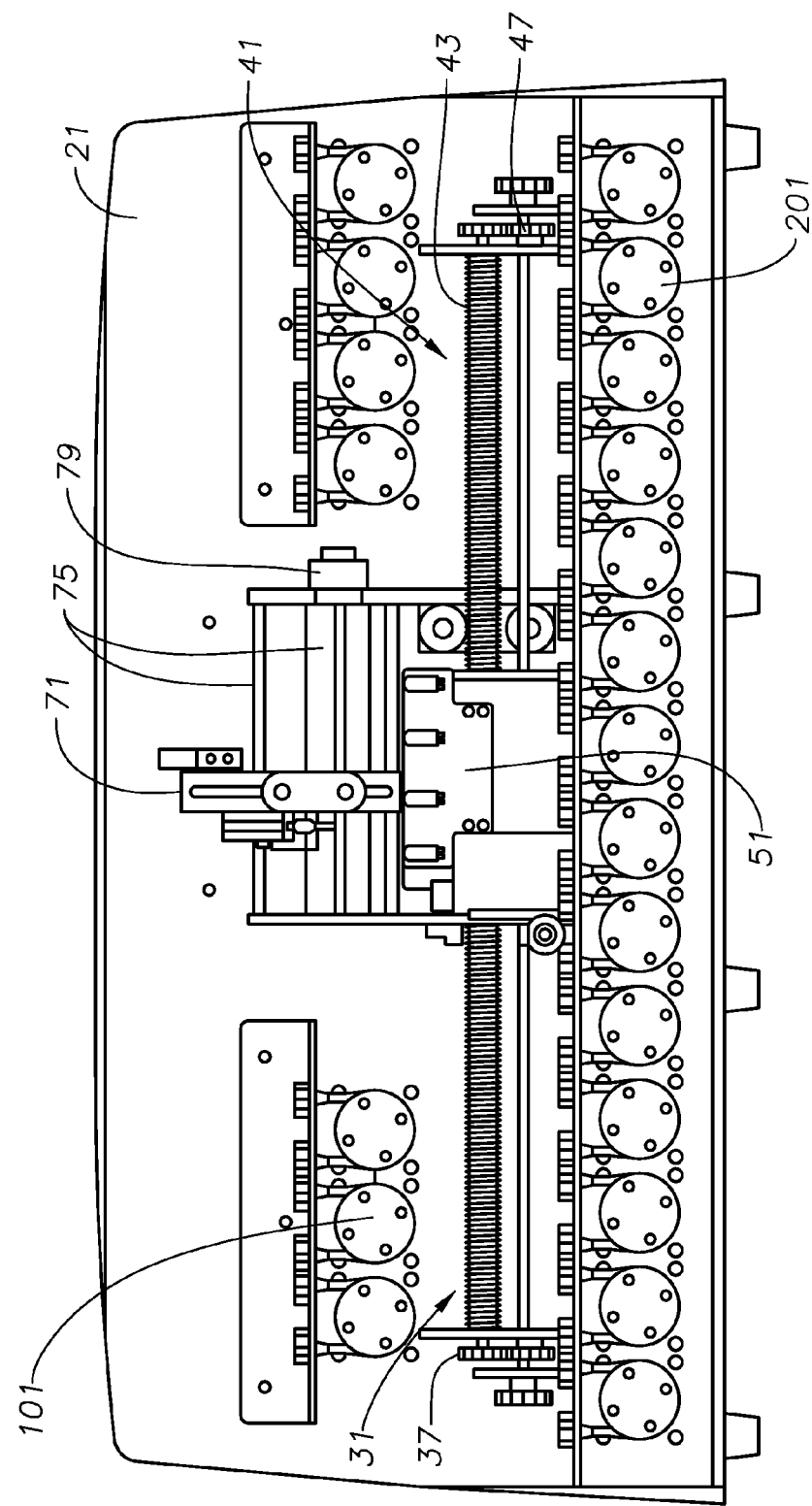

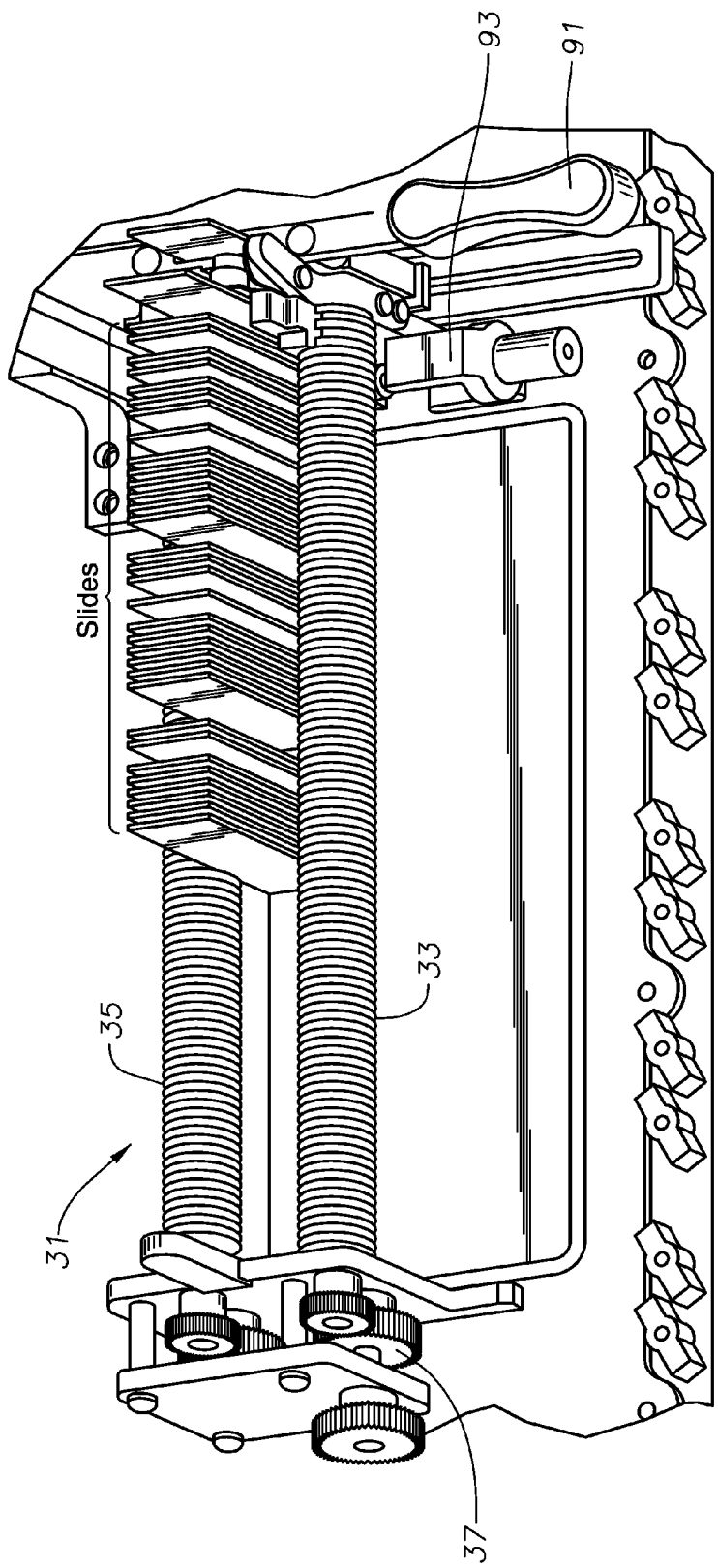

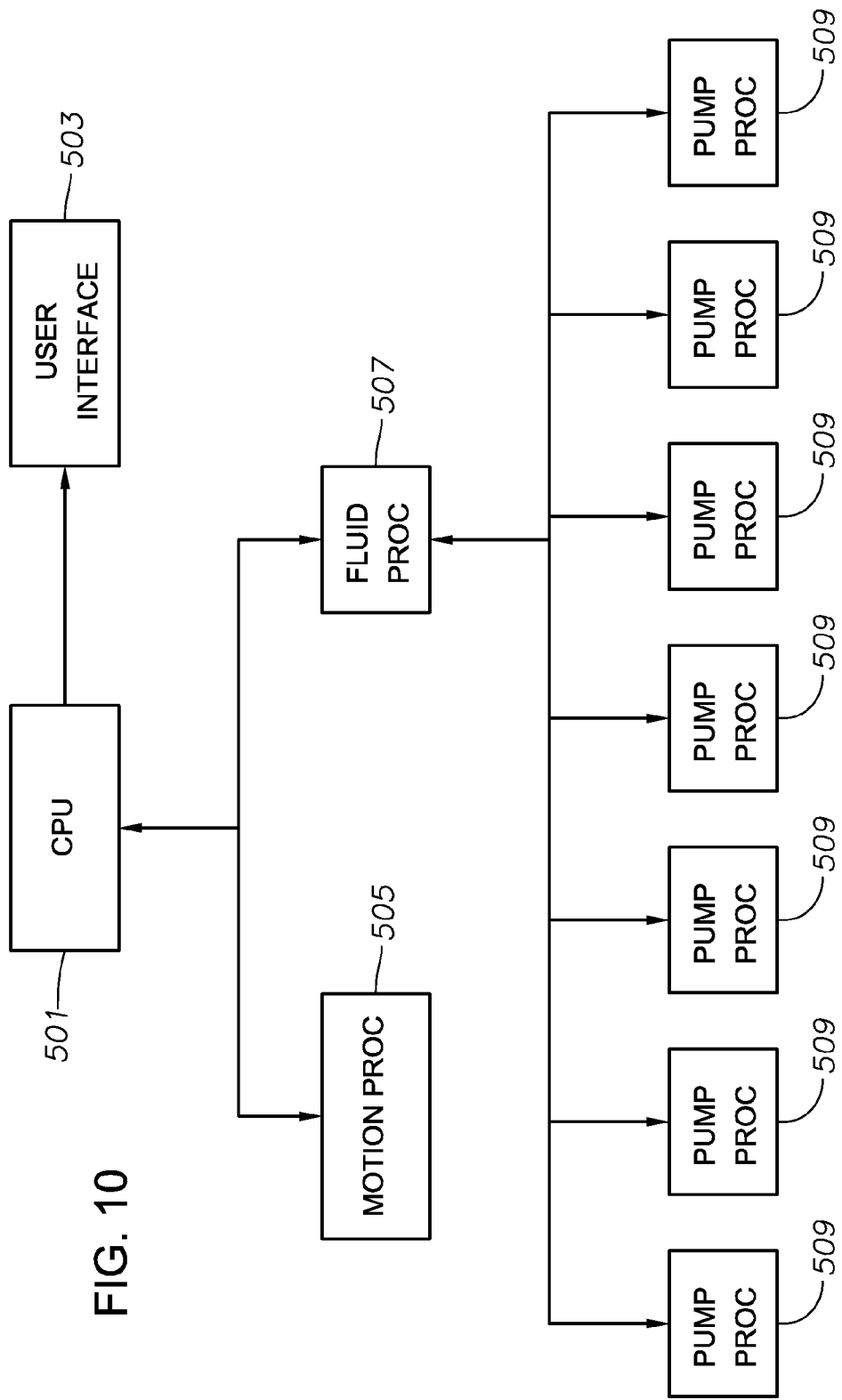

MULTIPLE SLIDE PROCESSING APPARATUS

CROSS-REFERENCE TO RELATED APPLICATIONS AND PRIORITY CLAIMS

This application is a continuation of application Ser. No. 13/857,965 filed Apr. 5, 2013, now U.S. Pat. No. 9,091,621, which is incorporated herein by reference for all purposes.

TECHNICAL FIELD

The present invention relates to apparatus for staining or other processing of microscope slides. More particularly, the present invention relates to apparatus for handling and processing multiple slides at once.

BACKGROUND OF THE INVENTION

Devices are known to automate the often tedious processing of microscope slides for analysis. For example, commonly assigned U.S. Pat. Nos. 7,452,506 and 6,468,764 disclose a method and apparatus for automated Gram staining of single microscope slides. The stainer disclosed in those patents is a single-slide variety: it can treat only one slide at a time. GGB Company LLC of Wichita Falls, Tex. sells a single-slide stainer embodying this technology under the model number AGS-1000, and it has proven to be a technical and commercial success, accurately staining thousands if not millions of microscope slides.

Other automated staining and processing apparatuses are known, some of which can handle multiple or more than one slide at a time. These multiple staining devices variously employ carousels or robot arms to move slides from station to station for application of reagents and the like. None, however, match the Gram stain accuracy of the AGS-1000.

A need exists for improved slide processing apparatus capable of performing slide processing operations on multiple or more than one microscope slide.

SUMMARY OF THE INVENTION

It is a general object of the present invention to provide a microscope slide staining or processing apparatus capable of processing multiple microscope slides. This and other objects of the invention are achieved with a slide processing apparatus comprising a slide or processing station which may include a plurality of cuvettes, each cuvette configured to receive a slide. A reagent fluid supply is coupled to each cuvette to deliver and apply reagent for treatment of the slide. A slide gripper is disposed above the slide processing station and is configured to move the slide in and out of the cuvettes. A screw assembly is disposed adjacent the slide processing station, the screw assembly configured to receive a plurality of slides, wherein rotation of the screw assembly advances the plurality of slides for engagement by the slide gripper.

According to a preferred embodiment of the invention, the screw assembly further comprises a pair of parallel, spaced-apart screws, each of the screws having threads. A motor and controller rotate each of the screws, wherein slides are placed between the screws with their edges engaged by the threads and controlled rotation of the screws moves the slides.

According to a preferred embodiment of the invention, the screw assembly further comprises a first screw assembly disposed on one side of the cuvettes and a second screw assembly disposed on an opposite side of the cuvettes, the first screw assembly for advancing untreated slides, the second screw assembly for advancing treated slides.

According to a preferred embodiment of the invention, the cuvettes further comprise a pair of cuvettes for applying crystal violet; a pair of cuvettes for applying Gram's iodine; a single cuvette to apply acid alcohol; and a pair of cuvettes to apply safranin, wherein application of crystal violet, Gram's iodine, acid alcohol and safranin can occur simultaneously.

According to a preferred embodiment of the invention, the slide gripper further comprises a pair of jaws mounted on linear bearings for horizontal movement above the cuvettes and between the cuvettes and the screw assembly.

Other objects, features and advantages of the present invention will become apparent with reference to the figures and the detailed description, which follow.

BRIEF DESCRIPTION OF THE DRAWINGS

FIG. 2 is a front elevation view of the apparatus with the shroud or cover removed.

FIG. 3 is an enlarged front elevation view of a portion of FIG. 2.

FIG. 10 is a block diagram depicting the controller for the slide processing apparatus according to the present invention.

DETAILED DESCRIPTION OF THE INVENTION

Figure 1:
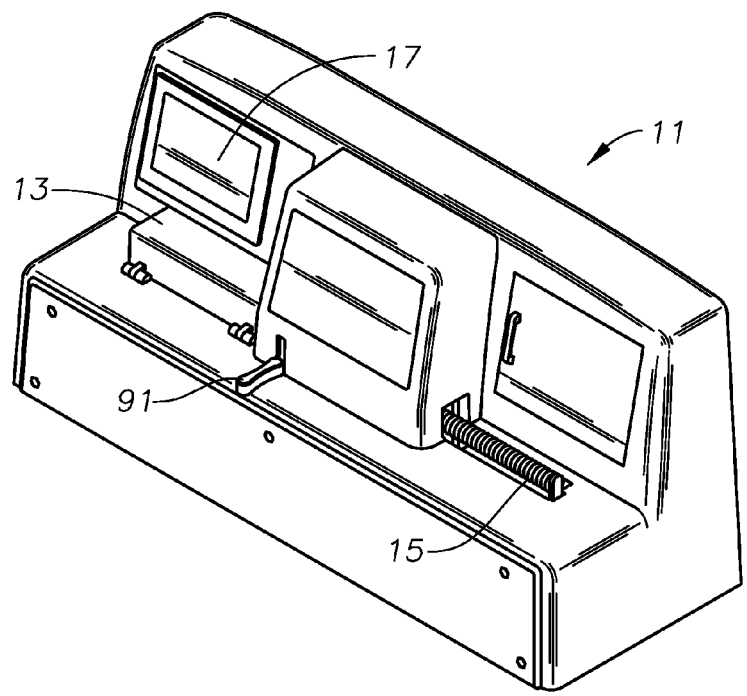
FIG. 1 is a perspective view of the apparatus according to the present invention.

Referring now to the Figures, and particularly to FIG. 1, a multiple-slide staining apparatus 11 according to an embodiment of the present invention is shown. The exterior of the device includes loading 13 and unloading 15 ports, through which microscope slides are loaded and unloaded, and a touch-screen monitor and input device 17 or user interface for accessing control functions of the apparatus. Various access panels may be provided.

FIG. 2 illustrates apparatus 11 with the shroud removed. A generally L-shaped (viewed from the end, see FIG. 5) panel mounts the various components of the slide stainer according to the present invention. First and second or load and unload screw assemblies 31 and 41 are mounted on panel 21 on either side of a slide processing station 51 and are driven by geared motors 37, 47. Load and unload screw assemblies 31, 41 hold the microscope slides and advance them toward or away from slide processing station 51. An arm 71 and gripper 73 remove the slides from the load screw assembly 31, place them selectively in slide processing station 51, and move them from station 51 to unload screw assembly 41.

FIG. 3 illustrates a first or load screw assembly 31. Each of the screw assemblies 31, 41 is similar and comprises a pair of parallel, spaced apart lead- or conveyor screws 33,

35. Microscope slides are captured or held between the threads of each pair of screws and controlled rotation by a geared motor 37 advances the slides toward slide processing station or cuvette assembly 51 (in the case of load screw assembly 31) and away from slide processing station 51 (in the case of unload screw assembly 41).

Each slide has a biological tissue or fluid sample or specimen applied to it. It is this specimen that is stained, processed, or treated by the apparatus according to the present invention, typically for microscopic analysis by a human technician. As shown, the plurality of microscope slides are preferably oriented "vertically," with one shorter end up and are maintained in a parallel, spaced-apart relationship while carried by screw assemblies 31, 41.

Although screw assemblies 31, 41 are illustrated as relatively permanently mounted to panel 21, they could also be part of a removable "cassette" assembly that permits loading and unloading of the cassette away from apparatus 11. Motors, gears, and controllers for rotating the screws in the cassette would preferably remain mounted on panel 21.

An arm assembly 71 is positioned above slide processing station or cuvette assembly 51 and has a slide gripper 73 that traverses on linear bearings 75 to grip or pick up a slide from load screw assembly 31, deposit the slide into a selected cuvette in slide processing station 51 for processing, and remove the slide from the selected cuvette and either deposit it in the next selected cuvette or into the threads of screw assembly 41 for storage of processed slides until they can be removed for analysis. Arm assembly 71 is powered by a motor 79.

A manual or bypass slide tray 91 is provided between screw assembly 31 and slide processing station 51. If the need arises to process a microscope slide that is not in the queue of load screw assembly 31, it can be placed in manual slide tray 91, which is provided with an optical sensor that senses the presence of a slide so that arm assembly can take the slide from tray 91 rather than load screw assembly 31.

A plurality of (seven) peristaltic reagent pumps 101 are associated with each of the seven cuvettes (FIG. 3). Peristaltic pumps are preferred because slide processing reagents can be corrosive and the pumps are by nature positive displacement, which permits metering of fluid quantity without use of separately controlled valves. These pumps are connected to reagent reservoirs (not shown, but preferably mounted on the reverse side of panel 21) and to cuvettes to supply reagent to each cuvette for slide processing. According to a preferred embodiment of the present invention, there are seven cuvettes and seven reagent pumps 101, each reagent pump 101 supplying reagent to a single cuvette.

There are also a plurality of water and drain peristaltic pumps 201 mounted underneath panel 21. Water pumps 201 are connected to a source of water and drain pumps 201 to a drain. Each of the water and drain pumps 201 (a total of 14) is connected to one of the seven cuvettes for rinsing and draining each cuvette as desired or necessary.

Reagent, water, and drain pumps 101, 201 are identical in configuration and capacity. Drain pumps 201 have their suction end in communication with the cuvette, rather than the discharge end, as in the case of reagent and water pumps. Drain pumps therefore remove fluid from the cuvettes rather than supply it, as in the case of reagent and water pumps. Preferably, drain pumps 201 are cycled forward and reverse to agitate rinse fluid in each cuvette prior to being actuated forward to drain or remove fluid from the cuvette. By using controlled positive-displacement pumps, the use of "wet" valves, and associated corrosion and reliability problems, is avoided. The only valves in the system are associated with the various pneumatically controlled elements (gripper 73 and kicker 93), which avoid the problems of valves exposed to liquids.

Figure 4:
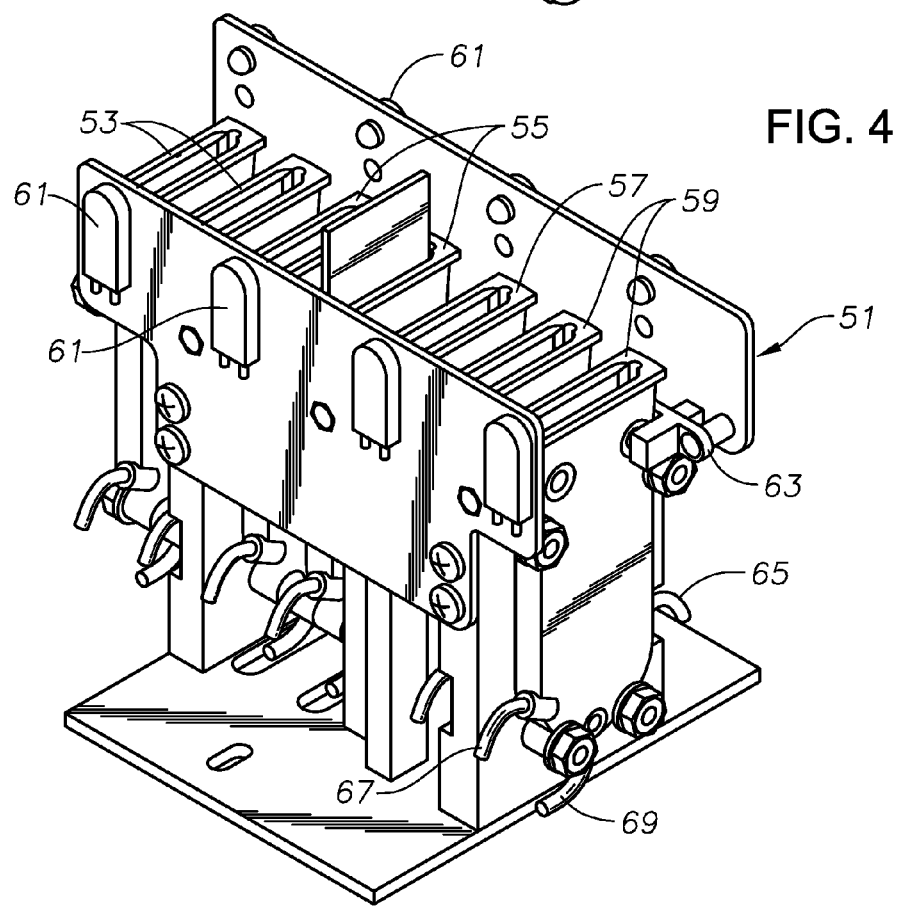
FIG. 4 is an enlarged perspective view of a portion of FIG. 2.

FIG. 4 is a perspective view of slide processing station or cuvette assembly 51, showing the seven cuvettes used in a preferred embodiment of the present invention. In the preferred embodiment of the invention, the slide processing technique is the Gram stain, which applies crystal violet (and rinses with water), then Gram's iodine (and rinses with water), followed by decolorizing with acid alcohol (and analysis of the decolorizing fluid to detect the level of staining in the slide specimen), and finished with safranin. In this preferred and illustrative embodiment, two cuvettes 53 are provided for crystal violet, two cuvettes 55 for Gram's iodine, one cuvette 57 for the acid alcohol decolorizing step (the fastest step), and another pair of cuvettes 59 for safranin. Gram stain processing occurs as disclosed in U.S. Pat. Nos. 7,452,506 and 6,468,764, which are incorporated herein by reference, with the optoelectronic detection of decolorization level, which indicates that a slide is properly stained. An optical sensor 61 is mounted adjacent and above each cuvette to detect the presence or absence of a slide in the cuvette. Although the illustrated and preferred embodiment processes microscope slides according to the Gram stain method disclosed in the foregoing patents, it can be easily adapted to perform other slide processing techniques, by changing the supplied reagents and/or number of cuvettes.

FIG. 4 also shows one of the seven cuvettes 59, which is exemplary of all of them. As can be seen, cuvette 59 is generally rectangular in configuration and has a recess or cavity opening at the upper end to receive a microscope slide. Cuvette 59 is connected by tubing 65 to one of the reagent pumps 101 for controlled delivery of a quantity of reagent (in the case of cuvette 59, safranin) to cuvette for slide treatment. Cuvette 59 is also connected by tubing 67 to a water pump 201 and water supply and by tubing 69 to a drain pump 201 and drain for respectively rinsing and draining cuvette 59. Optical sensors 63 are provided to detect the presence and level of reagent and rinse water in each cuvette and communicate that information to a computer controller.

Figure 5:
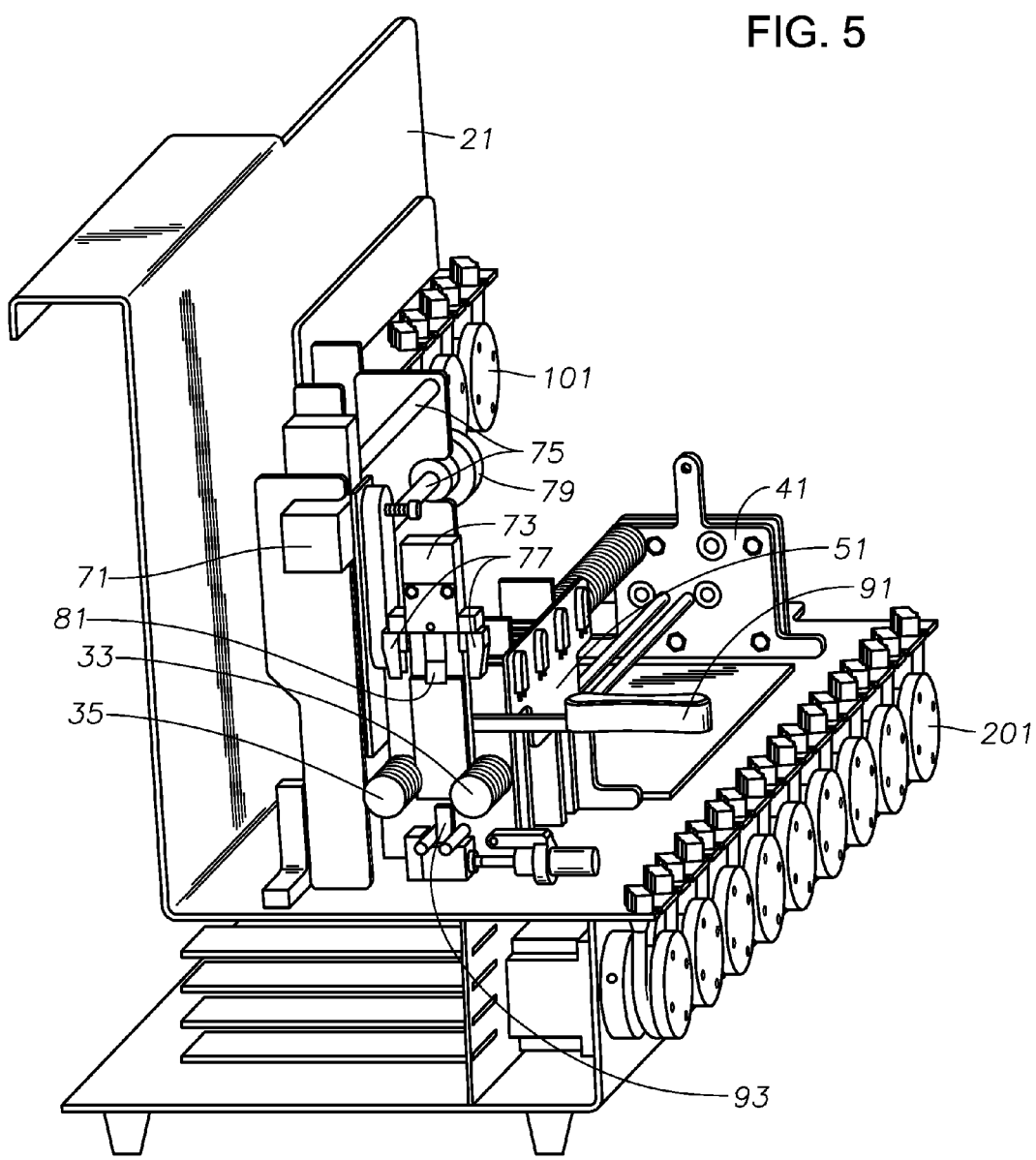
FIG. 5 is an end, fragmentary view of a portion of FIG. 2.

FIG. 5 illustrates arm 71 and gripper 73, which comprises a pair of opposing, horizontally moving jaws 77. As shown in FIG. 2, arm 71 is driven by a motor 79 and traverses horizontally on linear bearings 75 above slide processing station 51 and its cuvettes 53, 55, 57, 59 and between load and unload screw assemblies 31, 41. Jaws 77 move relative to one another to grip or engage the upper end of a microscope slide, remove it from first or load screw assembly 31, and deposit it in a sequence of cuvettes according to the slide processing sequence or algorithm.

A pneumatically operated kicker 93 is positioned below the slide in the ultimate or pick-up position of load screw assembly 31 to engage the bottom end of the microscope slide to raise the upper end of the slide for gripping by jaws 77 of slide gripper (a raised slide is shown in FIG. 2). When slide processing is complete, jaws 79 grip the upper end of the slide and deposit it between the threads of second or unload screw assembly 41 for storage until analysis.

Pumps 101, 201 are controlled and operated by electric stepper motors, as are load and unload screw assemblies 31, 41. Gripper 73 is controlled and operated pneumatically, as is slide kicker 93.

Figure 6:
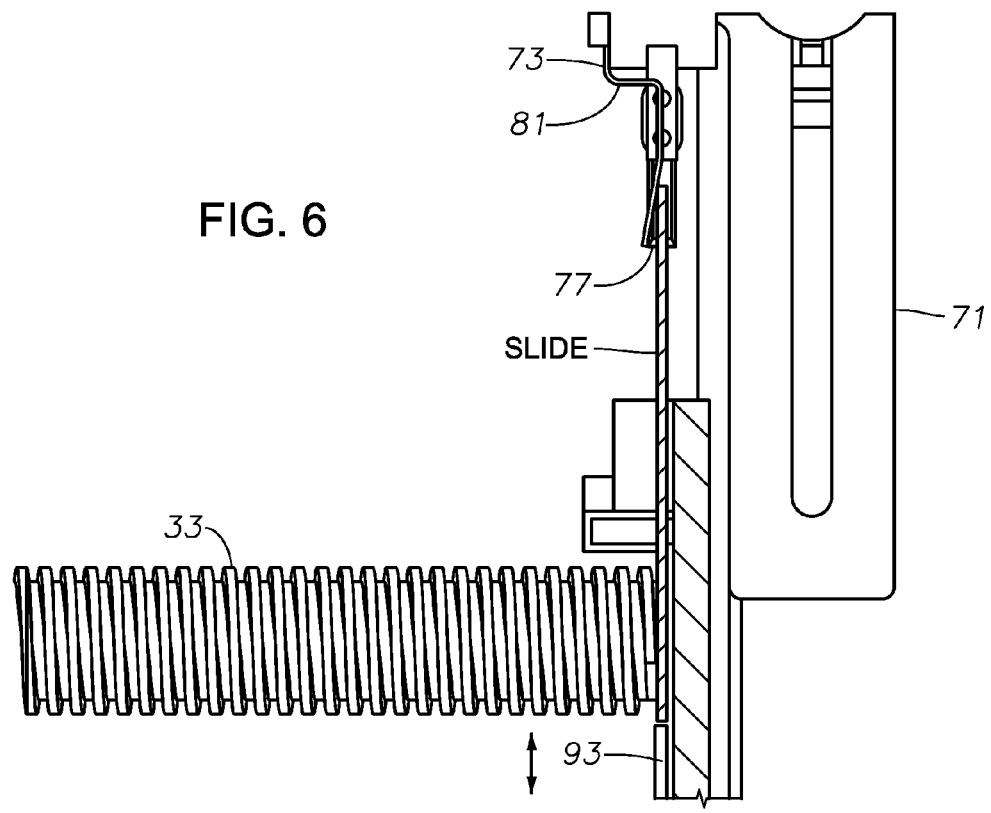
FIG. 6 is a side elevation view of a portion of FIG. 5.

FIG. 6 illustrates the relationship between gripper 73, a microscope slide, one of screws 33, 35 of screw assembly 31, and slide kicker 93 at the point where the slide is removed from load screw assembly 31, the ultimate or pickup position. A deflector 81 (see FIG. 5 also) formed of relatively resilient and flexible spring steel, is positioned between jaws 77 of gripper 33 to urge and maintain the slide in a vertical position so that its upper end can be grasped by jaws 77. Also, the upper portion of slide kicker 93 is shown in engagement with the bottom of the slide, raising it for engagement or gripping by jaws 77 of gripper 73.

Figure 7:
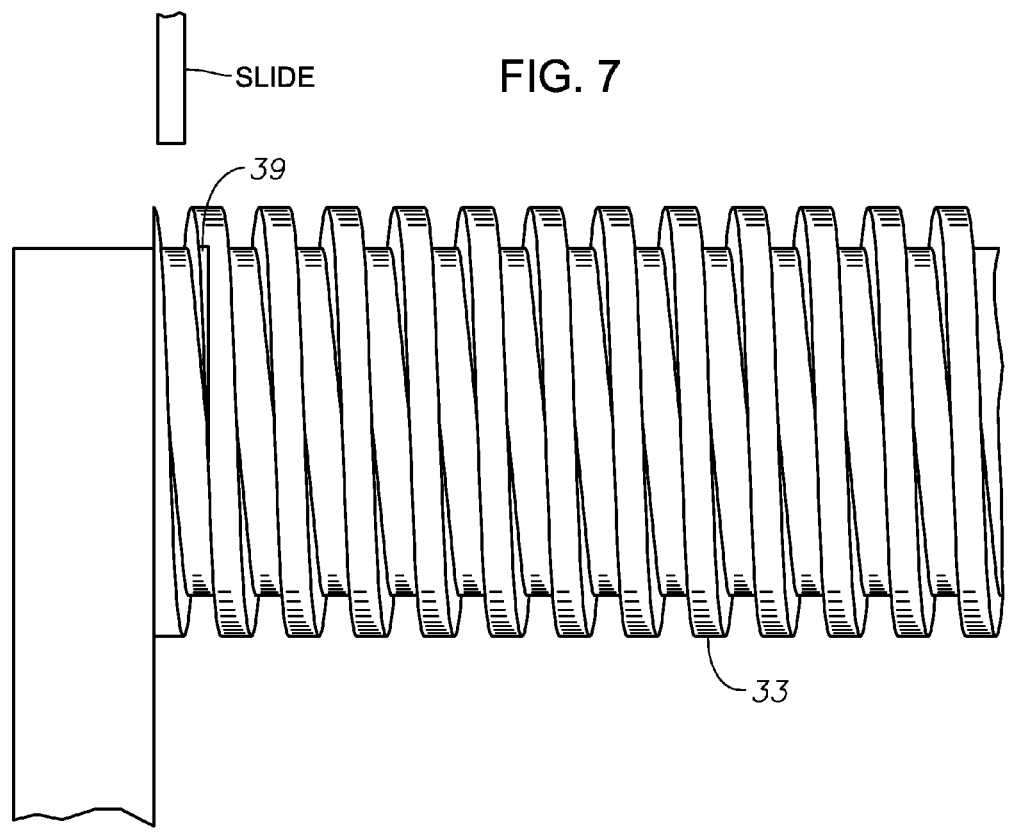
FIG. 7 is an enlarged view of a portion of FIG. 2.

FIG. 7 is an enlarged view of the end of one of screws 33, 35 of load screw assembly 31. Due to variation in the thickness of microscope slides, the space and angle or pitch between adjacent threads of screw 33 may permit or cause the slide to tilt forward, away from vertical. Deflector 81 described in FIG. 6 above helps return the slide to vertical for engagement by jaws 77 of gripper 73. A generally rectangular notch or recess 39 is provided in the leading face of the last full thread of each screw 33, 35 to provide "room" or clearance for the slide to be urged and maintained in the vertical position by deflector 81 without breakage.

Figure 8:
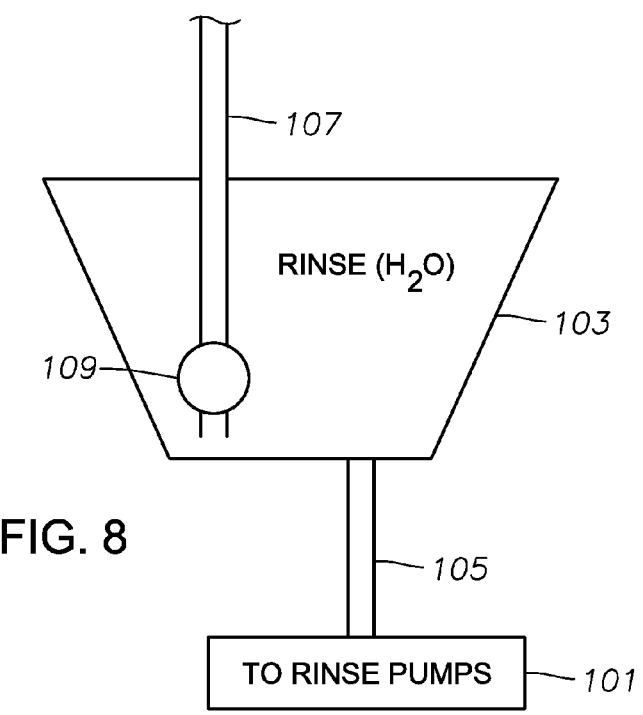
FIG. 8 is a schematic view of a rinse water reservoir according to the present invention.

FIG. 8 illustrates schematically a rinse water reservoir 103 according to the present invention. Reservoir 103 typically is a jug or other commercial container of deionized water that resides outside of the shroud or cover of apparatus 11. It is connected by one or more tubes 105 to the rinse water pumps 101. An air breather line 107 vents reservoir 103 to atmosphere and extends to the bottom of reservoir 103. Line 107 also includes a pneumatic pressure sensor 109. Sensor 109 detects pressure exerted on the air in line 107 by the hydrostatic pressure of water in reservoir 103. Sensor 109 is calibrated when reservoir 103 is empty and full of deionized water and periodically purges line 107 to insure accuracy. The hydrostatic pressure measured by sensor 109 corresponds to the fluid level in reservoir and sensor communicates this level to the controller to insure ready supply of rinse water and indicate when the reservoir needs replacement or refilling.

Figure 9:
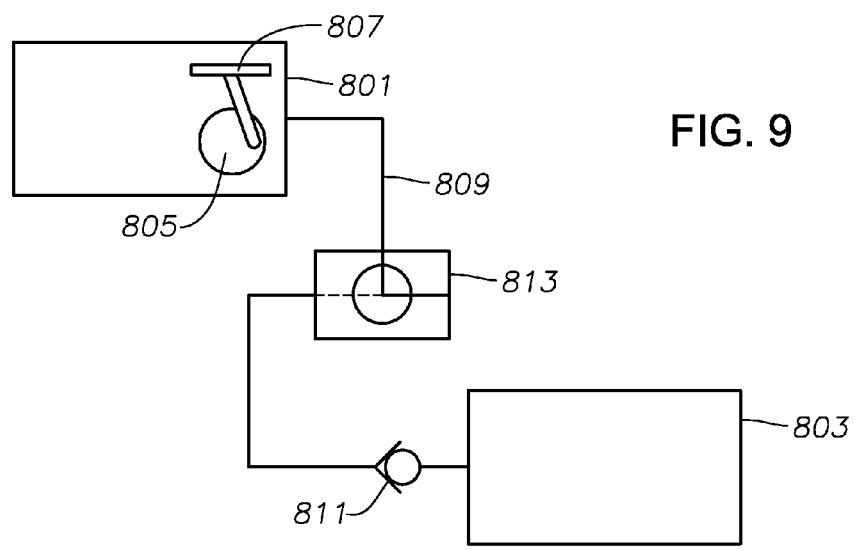
FIG. 9 is a schematic illustration of the pneumatic power source and reservoir according to the present invention.

FIG. 9 is a schematic depiction of the pneumatic power source and reservoir of the present invention that supplies pneumatic pressure or power to the various pneumatic components of slide processing apparatus 11, including and gripper 73 and slide kicker 93. A pump 801 pressurises a reservoir 803 to a pressure of approximately 28-30 psi. Pump assembly 801 includes an electric motor 805 connected by an eccentric to a reciprocating air pump 807 that provides pressurized air at 15-18 psi. The output of pump 801 is supplied to reservoir via a tube or conduit 809. A one-way check valve 811 is placed in conduit 809 to retain pressurized air in reservoir 803, while admitting further air in, permitting pressure to build in reservoir. A solenoid-operated two-position T valve 813 is placed in the conduit 809 between pump 805 and check valve 811. T valve 813 is switchable between an open position venting conduit 809 to atmosphere to depressurize the system and a closed position (indicated by the dashed line) coupling pump 801 to reservoir 803 to pressurize the reservoir. The solenoid of T valve 813 is in the same circuit as motor 805 current supply so that when motor is running, T valve 813 is in the closed position, and when it is not running, T valve 813 is in the open position, venting to atmosphere.

FIG. 10 is a high-level block diagram depicting the controller for the slide processing apparatus according to the preferred embodiment of the present invention. A CPU 501, preferably an ARM 9 microprocessor, provides central control over all functions of the apparatus according to the present invention and provides display functions to and accepts input from a user interface 503, which preferably is a touch-screen (17 in FIG. 1). CPU 501 is in two-way communication (RSC-232/C) with two second-level processors: a motion processor 505 and a fluid processor 507, both of which preferably are ARM 7 microprocessors.

Motion processor 505 controls the motion or movement of screw assemblies (31, 41 in FIG. 2) via their electric motors, as well as gripper 73, kicker 93, and pressure sensor 109, each of which is pneumatically operated. It is thus responsible for controlling movement of microscope slides through the apparatus according to the present invention. Motion processor 505 receives input from optical sensors 61, among others.

Fluid processor 507 is responsible for control of fluid supply (reagents, rinse water, drain functions) and the actual slide processing involving primarily the timing and quantity of fluids applied to the slide in the cuvettes, and operation of the decolorizing process. Fluid processor 507 receives input from sensors 63 and 109 and those similar sensors associated with reagent reservoirs, among others. Fluid processor 507 is in overall control of seven cuvette or pump processors 509.

Preferably, for the Gram stain process described above, there are seven pump processors 509, one for each of the seven cuvettes employed in the process. Each pump processor is preferably an 8051 Core microprocessor in bidirectional (preferably IIC) communication with a reagent pump 101 (more accurately its motor), a water or rinse pump 201, and a drain pump 201 associated with each cuvette. Thus, pump processors 509 control the operation of pumps 101, 201 and thereby the delivery of reagent and water to each cuvette and the draining of such fluids from the cuvette. Pump processors 509 and their circuit boards are identical and interchangeable.

In operation, slides are loaded vertically in load screw assembly 31, which then rotates to advance the slides toward processing station 51. Arm 71 and gripper 73 then take a slide from the ultimate or pick-up position in load screw 31 and place the slide in the first cuvette 53 (for application of crystal violet and rinse in the Gram stain example). Arm 71 and gripper 73 then return to load screw assembly 31, which has advanced another slide into the ultimate position. Arm 71 and gripper 73 then pick up that slide and move it into the second crystal violet cuvette 53. As the application of crystal violet completes (controlled by time and/or volume of reagent), the first slide is moved to the first Gram's iodine cuvette 55 and arm 71 and gripper 73 return to load screw 31 (which again has advanced) and places the third slide in the now-vacant first crystal violet cuvette 53. Arm 71 then moves between load screw 31 and cuvettes, moving slides from cuvette to cuvette as each process completes and filling the then-vacant cuvettes with a new slide for the next process. This operation proceeds, placing slides in alternating fashion through the crystal violet 53, Gram's iodine 55, and safranin cuvettes 59. The exception is the acid alcohol or decolorizing cuvette 57, which process occurs sufficiently quickly (roughly twice as fast as the crystal violet, Gram's iodine, and safranin processes, that is 15-30 seconds compared with 30-60 seconds) that each successive slide can be treated in one cuvette 57. Optical sensors 61 monitor which cuvettes are occupied and which are vacant. As the application of safranin concludes, the slide is picked up by arm 71 and gripper 73 and placed into the first or unload position in the unload screw assembly 41, which then advances to create a vacant first position for the next slide. If a single (or more) slide needs to be processed out of order, a slide can be loaded into bypass 91, where it will be transferred into a cuvette instead of the slide in the ultimate position of load screw assembly 31, and will be moved through the cuvettes in similar fashion. This process permits automated Gram staining at approximately one slide per minute or 60-70 per hour. As mentioned above, the apparatus according to the present invention can be adapted to other slide staining or treatment processes, achieving similar efficiency gains.

The invention has been described with reference to illustrative and preferred embodiments. It is thus not limited, but is susceptible to variation and modification without departure from the scope of the claims, which follow.

We claim:

1. A method of sequentially treating microscope slides using treatment processes of different duration comprising the steps of:
   placing a plurality of microscope slides in a corresponding plurality of first-process receptacles for treatment with a first treatment process;
   removing a first of the plurality of microscope slides from one of the first-process receptacles, creating a vacated receptacle;
   placing the first microscope slide in a second-process receptacle for treatment with a second treatment process, while other of the plurality of microscope slides undergo treatment with the first treatment process, wherein the second treatment process is of shorter duration than the first treatment process;
   replacing the first microscope slide with a new microscope slide in the vacated first-process receptacle;
   removing the first microscope slide from the second-process receptacle; and
   replacing the first microscope slide in the second-process receptacle with another of the plurality of microscope slides from the first-process receptacles.

2. The method according to claim 1, further comprising the steps of:
   after removing the first of the plurality of microscope slides from the second-process receptacle, placing the first microscope slide in a third-process receptacle for treatment with a third treatment process.

3. The method according to claim 1, wherein:
   the first treatment process is application of Gram's iodine to the microscope slide, and occurs in two first-process receptacles;
   the second treatment process is application of acid alcohol to the microscope slide and occurs in one second-process receptacle, and the application of acid alcohol is approximately half the duration of the application of Gram's iodine; and
   the third treatment process is application of safranin to the microscope slide and occurs in two third-process receptacles.

4. The method according to claim 3, further comprising:
   prior to the step of placing the plurality of microscope slides into the corresponding plurality of first-process receptacles, placing the plurality of slides into a pair of crystal violet receptacles for the application of crystal violet.

5. A method of sequentially Gram staining microscope slides using treatment processes of different duration comprising the steps of:
   placing a plurality of microscope slides in a corresponding plurality of Gram's iodine receptacles for treatment with Gram's iodine;
   removing a first of the plurality of microscope slides from one of the Gram's iodine receptacles, creating a vacated receptacle;
   placing the first microscope slide in an acid-alcohol receptacle for treatment with acid alcohol, while other of the plurality of microscope slides undergo treatment with the Gram's iodine, wherein the acid alcohol treatment is of shorter duration than the Gram's iodine treatment;
   replacing the first microscope slide with a new microscope slide in the vacated Gram's iodine receptacle;
   removing the first microscope slide from the acid alcohol receptacle; and
   replacing the first microscope slide in the acid alcohol receptacle with another of the plurality of microscope slides from the Gram's iodine receptacles.

6. The method according to claim 5, further comprising the steps of:
   after removing the first of the plurality of microscope slides from the Gram's iodine receptacle, placing the first microscope slide in a third-process receptacle for treatment with a third treatment process.

7. The method according to claim 6, wherein:
   the third treatment process is application of safranin to the microscope slide and occurs in two third-process receptacles.

8. The method according to claim 5, further comprising the step of:
   prior to the step of placing the plurality of microscope slides into the corresponding plurality of Gram's iodine receptacles, placing the plurality of slides into a pair of crystal violet receptacles for application of crystal violet.

* * * * *